US00PP36254P2

(12) United States Plant Patent
Hansen

(10) Patent No.: US PP36,254 P2
(45) Date of Patent: Nov. 19, 2024

(54) ***SPIGELIA* PLANT NAMED 'Apple Slices'**

(50) Latin Name: ***Spigelia* hybrid**
Varietal Denomination: Apple Slices

(71) Applicant: Hans A Hansen, Zeeland, MI (US)

(72) Inventor: Hans A Hansen, Zeeland, MI (US)

(73) Assignee: Walters Gardens, Inc., Zeeland, MI (US)

( * ) Notice: Subject to any disclaimer, the term of this patent is extended or adjusted under 35 U.S.C. 154(b) by 0 days.

(21) Appl. No.: 18/445,736

(22) Filed: Jan. 8, 2024

(51) Int. Cl.
*A01H 5/02* (2018.01)
*A01H 6/00* (2018.01)

(52) U.S. Cl.
USPC ..... Plt./263.1

(58) Field of Classification Search
USPC ..... Plt./263.1
See application file for complete search history.

(56) References Cited

PUBLICATIONS https://www.canr.msu.edu/news/where-can-i-learn-more-about-how-to-grow-this-crop. Retrieved from the Internet on May 15, 2024).*

* cited by examiner

*Primary Examiner* — Susan McCormick Ewoldt

(57) ABSTRACT

A unique cultivar of the *Spigelia* plant named 'Apple Slices' is characterized by vigorous, dense, upright, multi-stemmed, winter-hardy habit with dark-green, lanceolate leaves. Flowering begins in early June and continues for about four or five weeks, repeating in the fall. Petals are reddish on the outside and butter yellow with a slight blush of red on the inside. The new plant is especially suitable for a cut flower, for the landscape as a potted plant, and in the garden as a specimen or en masse.

2 Drawing Sheets

Botanical classification: *Spigelia* hybrid.
Variety denomination: 'Apple Slices'.

STATEMENT REGARDING PRIOR DISCLOSURES UNDER 37 CFR 1.77(b)(6)

The first non-enabling disclosure of the claimed plant, in the form of a photograph and brief description on a website operated by Walters Gardens, Inc. on Dec. 1, 2023. The new plant was first offered for sale on Jan. 9, 2023, and sold on May 22, 2023, to Dallas Johnson Greenhouses by Walters Gardens, Inc. No plants of *Spigelia* 'Apple Slices' have been sold or offered for sale anywhere in the world, nor has any disclosure of the new plant been made, more than one year prior to the filing date of this application, and such sale or disclosure within one year was either derived directly or indirectly from the inventor.

BACKGROUND OF THE INVENTION

The present invention relates to a new and distinct cultivar of *Spigelia* plant known as *Spigelia* 'Apple Slices' and will be referred to hereafter by its cultivar name, 'Apple Slices', or the "new plant". *Spigelia* is in the Loganiaceae family. The new plant was a self-pollination by the inventor at a wholesale perennial nursery in Zeeland, Michigan of the proprietary unreleased hybrid known only by the breeder code 12-5-4 (not patented). The new plant passed initial evaluation in the summer of 2017 and was assigned the breeder code 15-3-6 through the remaining evaluation process. 'Apple Slices' was first asexually propagated by shoot tip cutting in the spring of 2019 at the same nursery in Zeeland, Michigan. The unique characteristics of the new plant have been found to be reproducible and stable in successive generations of asexually propagated and the resultant plants are identical to the original selection.

BRIEF SUMMARY OF THE PLANT

*Spigelia* 'Apple Slices' is unique from all other *Spigelia* known to the inventor. The nearest comparison plants known to the inventor include: *Spigelia marilandica* 'Little Redhead' (not patented), *Spigelia marilandica* 'Ragin Cajun' (not patented) and 'Orange Slices' U.S. Plant Patent Application pending.

The parent has a flower that is not as dark red and the foliage is not as dark green.

'Little Redhead' has a taller habit with lighter green and the flowers are not as dark reddish colored. 'Ragin Cajun' has a slightly shorter and more rounded habit, the flower petals are more orangish-red on the outside and brighter yellow on the inside, and the foliage is lighter green. 'Orange Slices' has a more orangish-red on the outside and a slightly shorter habit.

*Spigelia* 'Apple Slices' differs from all other *Spigelia* known to the inventor in the following repeatedly observed traits in combination:

1. Vigorous plants of dense upright habit, producing clean, dark-green, lanceolate leaves.
2. Multiple, densely-arranged, upright racemes.
3. Flower beginning in early June for about four to five weeks and repeating in the fall.
4. Flowers of reddish on the outside with butter yellow and slight reddish blush on the inside.

5. Flower shape is tubular with only slight flaring petal apices.

BRIEF DESCRIPTION OF THE DRAWINGS

The photographs of the new plant demonstrate the unique traits of *Spigelia* 'Apple Slices' and the overall appearance of a three-year-old plant growing in a full-sun trial garden in Zeeland, Michigan. The colors in the drawings are as accurate as reasonably possible with color reproductions. Variations in ambient light spectrum, source, and direction may cause the appearance of minor differences in color.

DETAILED BOTANICAL DESCRIPTION

Figure 1:
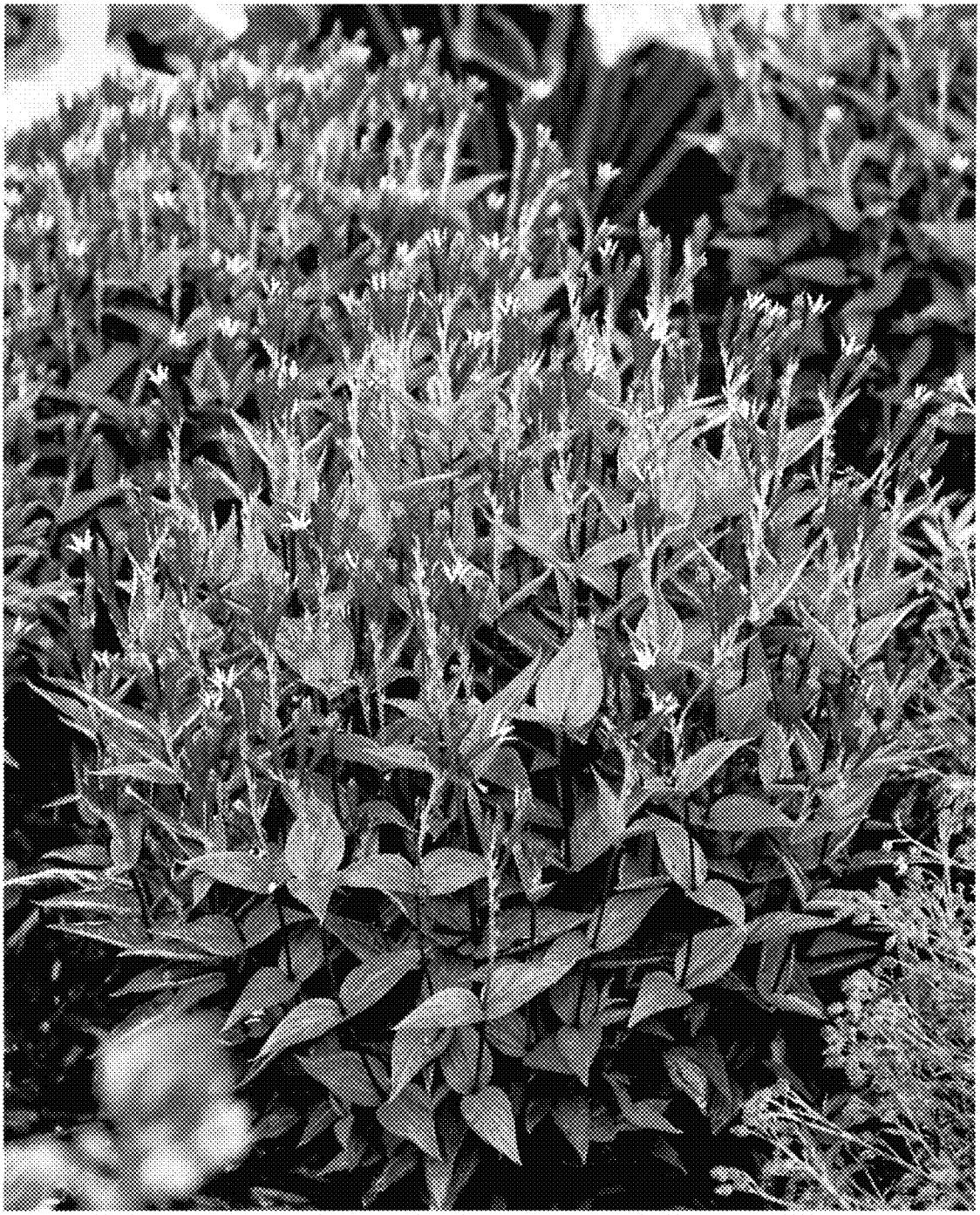
FIG. 1 shows a landscape habit view of the new plant in peak flower.
Figure 2:
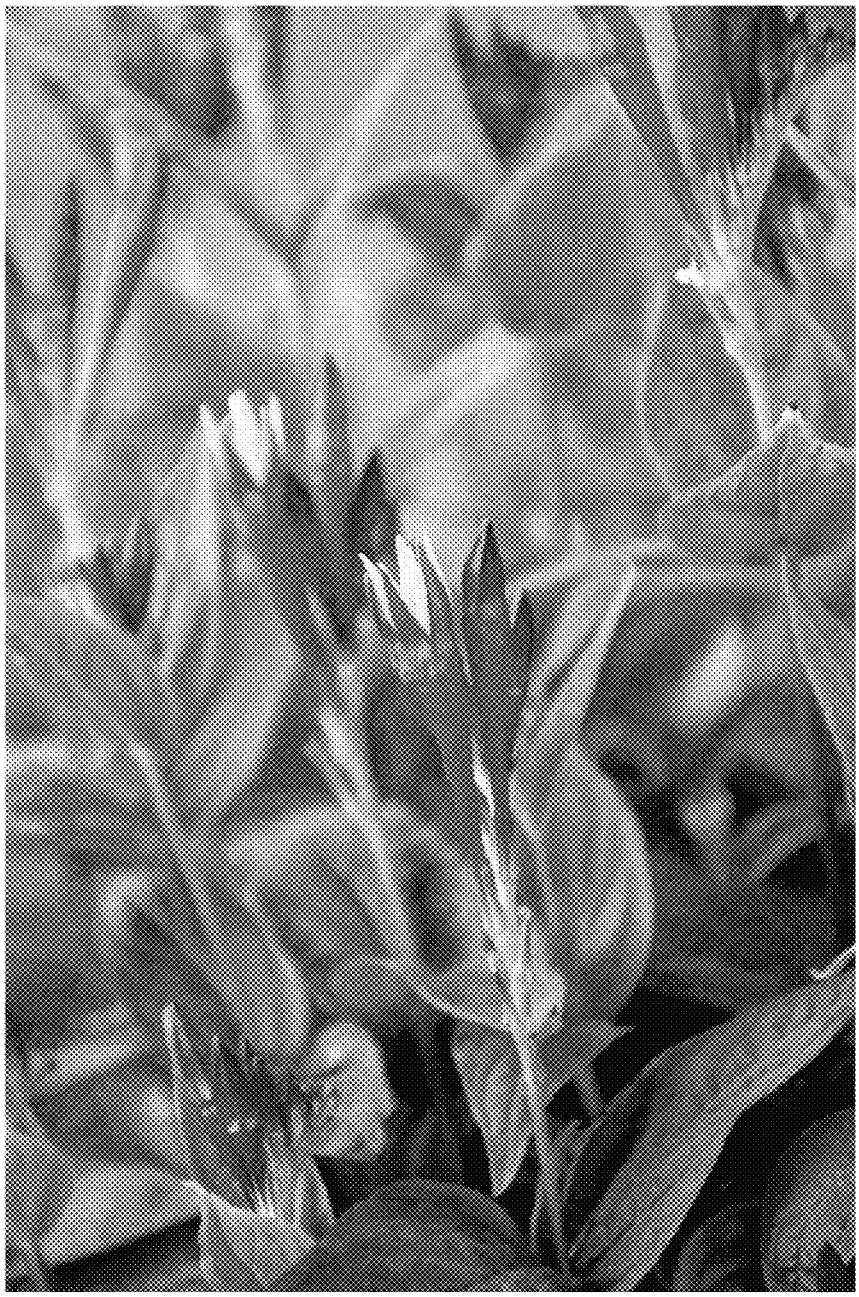
FIG. 2 shows a close-up of the flowers, buds, and foliage.

The following descriptions and color references are based on the 2015 edition of The Royal Horticultural Society Colour Chart except where common dictionary terms are used. *Spigelia* 'Apple Slices' has not been observed under all possible environments. The phenotype may vary slightly with different growing environments such as temperature, light, fertility, soil pH, moisture, and maturity levels, but without any change in the genotype. The following observations and size descriptions are based on three-year-old plants in a partially shaded greenhouse or a full-sun trial garden of a wholesale perennial nursery in Zeeland, Michigan with supplemental fertilizer and water as needed.

*Botanical classification.*—*Spigelia* hybrid.

*Parentage.*—parent is the proprietary hybrid known by the breeder code 12-5-4.

*Plant habit.*—winter-hardy, evergreen herbaceous perennial; dense, producing about 50 stiff, upright stems; flowering to about 57 cm tall and 50 cm wide.

*Propagation.*—stem cuttings; rooting in about 3 weeks.

*Time to produce finished crop in* 3.8-*liter pots.*—about 10 to 12 weeks; growth rate moderate.

*Root.*—fibrous and freely branching; to about 1 mm diameter; new root tip color creamy white, older roots pinkish-tan depending on soil type, nearest RHS N170D to RHS 174D.

*Leaves.*—simple; opposite; decussate; ovate; apex acute to narrowly acute; base truncate; sessile; margin entire; micro-puberulent both adaxial and abaxial.

*Leaf size.*—to about 8.4 cm long and 4.2 cm wide, average about 5.8 cm long and 3.2 cm wide.

*Leaf color.*—adaxial expanding between RHS 138B and RHS 137D and abaxial expanding between RHS 138C and RHS 139C; mature adaxial between RHS NN137A and RHS NN137B, mature abaxial nearest RHS 147B; lacking anthocyanin expression.

*Foliage fragrance.*—none detected.

*Veins.*—palmate; impressed adaxial and costate abaxial; puberulent to micro-puberulent adaxial and abaxial.

*Vein color.*—adaxial nearest RHS 146C, abaxial between RHS 146D and RHS 145C.

*Petiole.*—leaves sessile.

*Stems.*—cylindrical; stiff; upright; glabrous, limited branching below flowers; to about 47 cm long and 3.5 mm diameter at base.

*Stem color.*—between RHS 146D and RHS 138A in young distal portions with little sun exposure, developing to between RHS N186B and RHS N186C in proximal portions with high sun exposure;

*Nodes.*—about 7 nodes before flowers; average internode spacing about 6.7 cm.

*Node color.*—same color as surrounding stem.

*Inflorescence.*—upright; flowering in about the upper 12 cm and about 5 cm wide; about 10 to 14 flowers per inflorescence.

*Flowers.*—perfect; complete; tubular; apex slightly flared to about 21 mm across at apex and 47 mm long; with fused corolla tube about 42 mm long and 7 mm diameter below fusion; aspect upright.

*Flower longevity.*—about 5 days on plant; self-cleaning.

*Flower fragrance.*—none detected.

*Flowering period.*—beginning in early June and continuing for about four or five weeks, repeating in the fall.

*Buds one day prior to opening.*—narrowly clavate with inflated distal bulb portion gradually narrowing to base; acute apex with rounded base; bulb portion carinate between petals; to about 44 mm long, 6 mm diameter in terminal bulb portion, basal tube portion to about 1.5 mm diameter;

*Bud color.*—nearest RHS 53A distally and between RHS 53A and RHS 53B proximally.

*Petals.*—typically five, rarely six; lanceolate fused into corolla tube in the distal 36 mm; apex acute and only slightly flaring; margin entire; glabrous adaxial and abaxial.

*Petal size.*—to about 47 mm long and 4 mm wide just above fusion; fused in basal 36 mm forming tube, free in the distal 11 mm.

*Petal color.*—Adaxial: face margins nearest RHS 16D, face center nearest RHS 16D with a slight blush of nearest RHS 53A, corolla tube between RHS NN155A and RHS 53A. Abaxial: between RHS 53A and RHS 53B.

*Androecium.*—typically, five. Filaments: typically, five; cylindrical; glabrous; to about 31 mm long, adnate to inner corolla in proximal 25 mm and free in distal 6 mm, about 0.7 mm diameter; color nearest RHS NN155B; Anther: five; oblong elliptic; dorsifixed; longitudinal; introrse; about 3 mm long and 1 mm wide; color nearest RHS 6B. Pollen: nearly microscopic; color nearest RHS 2A.

*Gynoecium.*—one pistil per flower; 47 mm long. Style: cylindrical; straight; about 35 mm long and 0.7 mm diameter; persistent after flower abscission; color proximally nearest RHS 145C and distally nearest RHS 145C with moderate blush of nearest RHS 182D. Stigma: oblong; puberulent; 5 mm long, about 0.5 mm diameter; color nearest RHS 150D. Ovary: superior; ellipsoidal; glabrous; lustrous; about 2 mm long and 1.5 mm diameter; color nearest RHS 160B.

*Calyx.*—open, not fused; about 7 mm long and 3 mm across at apex.

*Sepals.*—five; linear; narrowly acute apex; base truncate, not fused; adaxial and abaxial slightly lustrous; margin entire; individually about 7 mm long and 1 mm wide at base.

*Sepal color.*—adaxial nearest RHS 145C proximally and nearest RHS 145A distally; abaxial nearest RHS.

*Peduncle*.—glabrous; stiff; upright; cylindrical; rarely branched; to 12 cm long and 2 mm diameter about distal leaves.

*Peduncle color*.—nearest RHS 145A with faint anthocyanin blush between RHS N186C and RHS N186B in portions receiving high sun exposure.

*Pedicle*.—cylindrical; glabrous; upright; to 3 mm long and 1.2 mm diameter, decreasing to about 1 mm long distally.

*Pedicle color*.—nearest RHS 145C.

*Fruit*.—two-lobed capsule, circumscissile at base; to about 5 mm and 3 mm across; color at maturity nearest RHS N200A.

*Seeds*.—one or two per ovary; spherical; asperous; to about 2 mm diameter; color nearest RHS N200A.

*Hardiness and culture*.—the new plant grows best with full sun, light moisture and deep drainage; hardy to at least from USDA zone 5b through 9.

*Disease and pest resistance*.—*Spigelia* 'Apple Slices' shows no susceptibility or resistance to pests or diseases that is not common to *Spigelia*.

I claim:

1. A new and distinct cultivar of *Spigelia* plant named 'Apple Slices', as herein described and illustrated.

* * * * *